United States Patent

Seng et al.

[11] 4,080,502
[45] Mar. 21, 1978

[54] 2,4-DIOXO-HEXAHYDRO-1,3,5-TRIAZINES

[75] Inventors: Florin Seng, Schildgen, Germany; Kurt Ley, deceased, late of Odenthal-Gloebusch, Germany, by Gertrud Elisabeth Luise Ley, heiress

[73] Assignee: Bayer Aktiengesellschaft, Leverkusen, Germany

[21] Appl. No.: 643,577

[22] Filed: Dec. 22, 1975

[30] Foreign Application Priority Data

Dec. 21, 1974 Germany .............................. 2460823
Dec. 21, 1974 Germany .............................. 2460824

[51] Int. Cl.² .......................................... C07D 251/10
[52] U.S. Cl. ................................................... 544/223
[58] Field of Search .................. 260/248 NS; 544/223

[56] References Cited

U.S. PATENT DOCUMENTS 3,035,055 5/1962 Slezak et al. ......................... 544/223
3,040,044 6/1962 Hirsch et al. ........................ 544/223

Primary Examiner—John M. Ford
Attorney, Agent, or Firm—Burgess, Dinklage & Sprung

[57] ABSTRACT

Compounds of the formula are disclosed:

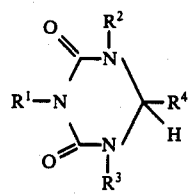

wherein
$R^1$, $R^2$ and $R^3$ are identical or different and represent an optionally substituted alkyl, alkenyl, cycloalkyl or an aryl group and
$R^4$ represents a monosubstituted or polysubstituted aryl group, containing at least one substituent which favours electrophilic aromatic substitution.

4 Claims, No Drawings

2,4-DIOXO-HEXAHYDRO-1,3,5-TRIAZINES

BACKGROUND

This invention relates to new aminals of aromatic aldehydes, obtainable by reaction of 2,4-dioxo-tetrahydro-1,3,5-triazinium salts, a process for the production of the aminals and to a process for the preparation of the corresponding aldehydes.

SUMMARY

The new compounds are characterized by the general formula

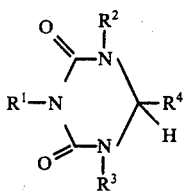

wherein
$R^1$, $R^2$ and $R^3$ are identical or different and represent an optionally substituted alkyl, alkenyl, cycloalkyl or an aryl group and
$R^4$ represents a monosubstituted or polysubstituted aryl group, containing at least one substituent which favours electrophilic aromatic substitution.

DESCRIPTION

For $R^1$, $R^2$ and $R^3$ there should be mentioned as examples of possible alkyl groups: aliphatic radicals with 1 to 18 carbon atoms, preferably with 1 to 4 carbon atoms, such as the ethyl, propyl, isopropyl, butyl, isobutyl, tertiary butyl and especially the methyl radical.

As substituents for these alkyl radicals there are mentioned halogen atoms such as fluoro, chloro and bromo atoms; the nitril group; $C_1$–$C_4$-alkoxy groups such as methoxy and ethoxy groups; carb-$C_1$–$C_4$-alkoxy groups such as carbmethoxy and carbethoxy groups; furthermore phenyl radicals which may be substituted by $C_1$–$C_4$-alkyl, cyano, halogen atoms, $C_1$–$C_4$-alkoxy. Examples of such substituted alkyl groups are: 2-cyanoethyl, 2-carbathoxy ethyl, 3-hydroxypropyl, 4-methoxybutyl, benzyl, 3-chloro-benzyl, 4-methyl-benzyl radicals.

As possible alkylene groups: mono-unsaturated or poly-unsaturated, preferably mono-unsaturated, aliphatic radicals with 2 to 10 carbon atoms, preferably 2 to 5 carbon atoms, such as the vinyl, the isomeric propenyl, butenyl and pentenyl radicals and especially the allyl radical.

As possible cycloalkyl groups: those with 5 to 12 carbon atoms, preferably with 5 or 6 carbon atoms, such as the cycloheptyl, cyclooctyl, cyclononyl, cyclododecyl and especially the cyclopentyl and cyclohexyl radical. As substituents for these cycloalkyl radicals there are mentioned especially $C_1$–$C_4$-alkyl such as methyl or tert.-butyl or halogens such as chlorine or bromine.

Preferred possible aryl groups are the phenyl or naphthyl radical. As substituents, especially for the phenyl radical, there are mentioned halogens such as fluorine, chlorine or bromine; $C_1$–$C_4$-alkyl radicals; substituted alkyl radicals such as the trifluoromethyl and chloromethyl group; the nitril group; carb.-$C_1$–$C_4$-alkoxy groups such as carbmethoxy and carbethoxy; and $C_1$–$C_4$-alkoxy groups such as methoxy and ethoxy.

Examples of substituted phenyl radicals are the chlorophenyl, cyanophenyl, methylphenyl, dimethylphenyl and tert.butylphenyl radicals.

For $R^4$ there are mentioned as representatives of the monosubstituted or polysubstituted aryl groups mono- or polysubstituted phenyl and naphthyl radicals.

Substituents favouring electrophilic aromatic substitution are for example $C_1$–$C_6$-alkyl groups such as methyl, ethyl, sec.-butyl, and n-hexyl; $C_1$–$C_6$-acylamino groups such as acetylamino, propionylamino and butyrylamino; especially however the hydroxy group, $C_1$–$C_4$-alkoxy groups, such as methoxy and ethoxy; and amino groups which may be mono- or disubstituted by $C_1$–$C_6$-alkyl radicals, such as N-methylamino, N,N-dimethylamino, N-ethylamino, N,N-diethylamino, N-butylamino, N,N-bis-(2-cyanoethyl)-amino, N,N-bis-hexylamino. Preferred substituents are the hydroxy and the amino groups.

The phenyl and naphthyl radical may contain besides the substituents favouring electrophilic aromatic substitution also other substituents for example halogen atoms such as fluorine, chlorine or bromine atoms; the nitrile group; and carb-$C_1$–$C_4$-alkoxy groups such as carbmethoxy or carbethoxy.

The process for the preparation of aminals of aromatic aldehydes of the general formula I comprises reacting 2,4-dioxo-1,2,3,4-tetrahydro-1,3,5-triazinium salts of the general formula

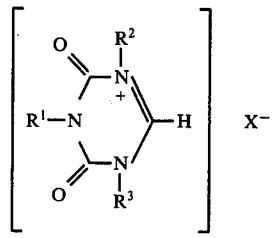

(II)

wherein
$X^-$ represents a chloride or bromide ion and $R^1$, $R^2$ and $R^3$ have the meaning indicated in formula I
with an aromatic compound of the general formula $R^4$—H, wherein
$R^4$ has the meaning indicated in general formula I.

The following may be mentioned as examples of 2,4-dioxo-1,2,3,4-tetrahydro-1,3,5-triazinium salts: 1,3,5-trimethyl-, 1,5-diethyl-3-methyl-, 1,5-dicyclohexyl-3-methyl-,1,5-dimethyl-3-isopropyl-, 1,5-diisopropyl-3-methyl-, 1,5-dibenzyl-3-methyl-, 1,5-dimethyl-3-phenyl-, 1,5-di-(3-trifluoromethyl-phenyl)-3-methyl-, 1-phenyl-3,5-dimethyl-, 1-(3-trifluoromethyl-phenyl)-3,5-dimethyl-, 1-(3-trifluoromethyl-4-chlorophenyl)-3,5-dimethyl-, 1,5-di-(carbomethoxymethyl)-3-methyl-, 1,5-di-(cyanomethyl)-3-methyl-, 1,5-dicyclopentyl-3-methyl-, 1,5-di-tert.-butyl-3-methyl-, 1,5-diallyl-3-methyl-, 1,5-di-n-butyl-3-methyl-, 1,5-di-isobutyl-3-methyl-, 1,5-di-n-propyl-3-methyl-, 1,5-di-(4-methoxybenzyl)-3-methyl-, 1,5-di(carboethoxy-methyl)-3-methyl-, 1,5-distearyl-3-methyl- and 1,5-di-dodecyl-3-methyl-2,4-dioxo-1,2,3,4-tetrahydro-s-triazinium chloride or bromide. The abovementioned compounds which are substituted by alkane radicals with 1 to 4 carbon atoms in the 1-, 3- and 5-position are preferred; 1,3,5-trimethyl-2,4-dioxo- 1,2,3,4-tetrahydro-s-triazinium bromide or chloride is particularly preferred.

Examples of aromatic compounds of the general formula R⁴-H are especially anilines or phenols which are optionally monosubstituted or polysubstituted at the aromatic ring by $C_1$-$C_4$-alkyl radicals, by halogen, cyano, carb-$C_1$-$C_4$-alkoxy or by a further hydroxyl or amino group, as well as anilines or phenols of which the amino group or hydroxyl group, respectively, is substituted by $C_1$-$C_4$ alkyl radicals or acyl radicals, preferred representatives of these anilines, and phenols are:aniline, N-methylanilne, N,N-dimethylanilene, N ethylaniline, N,N-diethylaniline, N-acetylaniline, 2-chloroaniline, 2-methylaniline, phenol, methoxybenzene, ethoxybenzene, 3-aminophenol 3-aminomethoxybenzene, 3-acetylaminophenol, 1,3-dihydroxybenzene, 1,2-dihydroxybenzene, 1,3-diaminobenzene, 1-naphthol, 2naphthol and 1-naphthylamine. 3-Aminophenol, 3-aminomethoxybenzene and 3-acetylaminophenol are particularly preferred.

The reaction according to the invention of the 2,4-dioxo-1,2,3,4-tetrahydro-1,3,5-triazinium salts with phenols and anilines is carried out depending on the reactivity of the reactants, especially of the aromatic compound, in general at temperatures of 0° C to 100° C. The process according to the invention can in principle be carried out with and without solvent. However, it has proved advantageous to carry out the reaction in a diluent which is inert under the reaction conditions. Examples of diluents which may be mentioned are water, lower aliphatic alcohols, such as, for example, methanol, ethanol and n- and iso-propanol, nitriles such as, for example, acetonitrile, nitrile, propionitrile, or benzonitrile, ethers such as, for example, diethyl ether, tetrahydrofurane and dioxane, as well as pyridine and formamides, such as, for example, formamide, N-methylformamide and dimethylformamide.

In the process according to the invention, hydrogen halide is liberated; this is suitably neutralised by addition of stoichiometric amounts of a base such as, triethylamine, sodium hydroxide, sodium carbonate or sodium bicarbonate. The function of the base can, of course, also be assumed, where appropriate, by suitable substituents of the aromatic compound, such as, amino groups, in which case the particular hydrohalide is formed.

The process according to the invention for the preparation of the animals of formula I may be explained by the reactions of 2,4-dioxo-tetrahydro-1,3,5-trimethyl-traizinium bromide with α-naphthol or aniline:

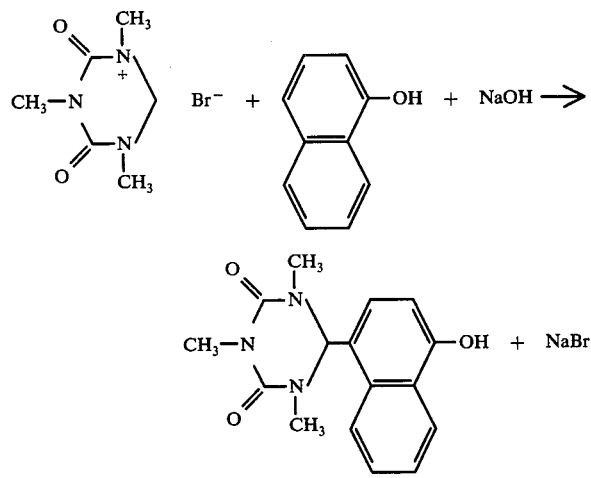

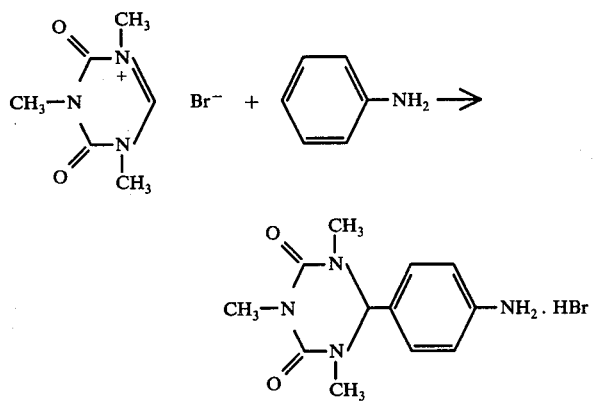

In practice, the process according to the ivention can, for example, be carried out as follows: the 2,4-dioxotetrahydro-1,3,5-triazinium salt is dissolved or suspended in a diluent and the aromatic compound and, if appropriate, the base are added. The aminal formed is isolated in the usual manner by filtration, precipitation or evaporation of the reaction solution. If aromatic amines are employed in the reaction, the corresponding aminehydrohalides are obtained as the product. They can be converted to the free compounds in a known manner, for example by treatment with sodium bicarbonate.

The following may be mentioned as examples of aminals which are obtained in accordance with the process of the invention: 6-(4-hydroxyphenyl)-, 6-(4-methoxyphenyl)-, 6-(4-aminophenyl)-, 6-(4-methylaminophenyl)-, 6-(4-ethylaminophenyl)-, 6-(4-dimethylaminophenyl)-, 6-(4-diethylaminophenyl)-, 6-(4-acetylaminophenyl)-, 6-(4-amino-2-chlorophenyl)-, 6-(4-amino-2-methylphenyl)-, 6-(4-amino-2-hydroxyphenyl)-, 6-(4-amino-2-methoxyphenyl)-, 6-(4-acetylamino-2-hydroxyphenyl)-, 6-(4-hydroxynaphthyl)- and 6-(2-hydroxynaphthyl)-1,3,5-trimethyl-2,4-dioxo-hexahydro-s-triazine, also 6-(4-aminophenyl)-, 6-(4-amino-2-chlorophenyl)- and 6-(4-amino-2-hydroxyphenyl)-1-methyl-3,5-diethyl-2,4-dioxo-hexahydro-s-triazine, also 6-(4-methylaminophenyl)-, 6-(4-diethylaminophenyl)- and 6-(4-amino-2-methoxyphenyl)-1-methyl-3,5-dicyclohexyl-2,4-dioxo-hexahydro-s-triazine and also 6-(4-ethylaminophenyl)-, 6-(4-amino-2-hydroxyphenyl)- and 6-(4-acetaminophenyl)-1-isopropyl-3,5-dimethyl-2,4-dioxo-hexahydro-s-triazine.

The 2,4-dioxotetrahydro-1,3,5-triazinium salts of the general formula II used as the starting material for the process according to the invention can be obtained by halogenating 2,4-dioxohexahydro-1,3,5-triazines of the general formula

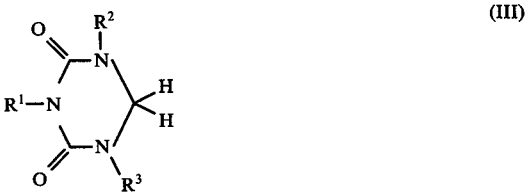

(III)

wherein
 R¹, R² and R³ have the meaning mentioned in formula I.

The invention therefore also concerns 2,4-dioxotetrahydro-1,3,5-triazinium salts of formula II and their production by halogenating the 2,4-dioxo-hexahydro-1,3,5-triazines of formula III.

As halogenating agent for the halogenation reaction, there can be used elementary halogen, especially chlorine or bromine or compounds which eliminate chlorine or bromine under the reaction conditions. Such compounds are, in particular, sulphuryl chloride, sodium hypochlorite or sodium hypobromite, tert.butyl hypochlorite, N-bromosuccinimide or sodium dichlorocyanurate.

The halogenation reaction is in general carried out at temperatures of 0° to 100° C, preferably at 20° to 50° C.

In some cases it has proved advantageous to carry out the halogenation in the presence of suitable diluents which are inert under the reaction conditions. Examples of diluents which can be used are lower aliphatic chlorohydrocarbons, such as methylene chloride, chloroform and carbon tetrachloride, lower aliphatic alcohols, such as methanol, ethanol, n- and iso-propanol and the like, ethers such as diethyl ether, tetrahydrofurane and dioxane, aliphatic and aromatic hydrocarbons, pyridine or water.

The halogenating agents are applied in general in amounts of 1 to 2 mol per mol 2,4-dioxo-hexahydro-1,3,5-triazine.

The 2,4-dioxo-hexahydro-1,3,5-triazines of the general formula III can be prepared by reaction of the biurets, suitably substituted in the 1-, 3- and 5-position, with aldehydes in the presence of acid catalysts. The biurets on their part are obtainable from the corresponding ureas and isocyanates in accordance with the reaction of N,N-dimethyl-urea and methyl-isocyanate described in Berichte 56, (1923) page 1914.

Examples which may be mentioned of 2,4-dioxotetrahydro-1,3,5-triazines which are employed preferentially for the halogenation are: 1,3,5-trimethyl-, 1,5-diethyl-3-methyl-, 1,5-dicyclohexyl-3-methyl-, 1,5-dimethyl-3-isopropyl-, 1,5-diisopropyl-3-methyl-, 1,5-dibenzyl-3-methyl-, 1,5-dimethyl-3-phenyl-, 1,5-di-(3-trifluoromethyl-phenyl)-3-methyl-, 1-phenyl-3,5-dimethyl-, 1-(3-trifluoromethyl-phenyl)-3,5-dimethyl-, 1-(3-trifluoromethyl-4-chlorophenyl)-3,5-dimethyl-, 1,5-di-(carbomethoxymethyl)-3-methyl-, 1,5-di-(cyanomethyl)-3-methyl-, 1,5-dicyclopentyl-3-methyl-, 1,5di-tert.-butyl-3-methyl-, 1,5-diallyl-3-methyl-, 1,5-di-n-butyl-3-methyl-, 1,5-di-isobutyl-3-methyl-, 1,5-di-n-propyl-3-methyl-, 1,5-di-(4-methoxybenzyl-3-methyl-, 1,5-di-(carboethoxy-methyl)-3-methyl-, 1,5-distearyl-3-methyl- and 1,5-di-dodecyl-3-methyl-2,4-dioxo-hexahydro-s-triazine.

The preparation of the 2,4-dioxo-1,2,3,4-tetrahydro-1,3,5-triazinium salts of the formula II used as the starting material may be explained by the reaction of 2,4-dioxohexahydro-1,3,5-trimethyl-triazine with bromine to give 2,4-dioxo-1,2,3,4-tetrahydro-1,3,5-trimethyl-triazinium bromide:

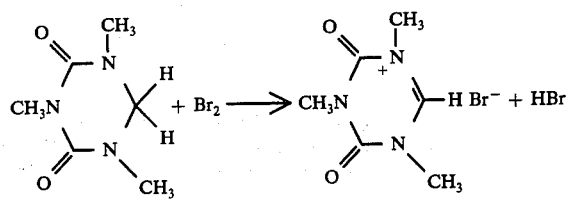

This reaction can be carried out by dissolving or suspending 2,4-dioxo-hexahydro-1,3,5-triazine in an inert diluent and adding the halogenating agent at temperatures of 0° to 100° C preferably 20° to 50° C. The reaction is generally complete after 1 to 5 hours. Thereafter the 2,4-dioxo-1,2,3,4-tetrahydro-1,3,5-triazinium salt is isolated in the usual manner by filtration, precipitation by addition of a non-polar solvent in which the salts are insoluble, or evaporation of the reaction solution. The reaction products can at times contain adsorbed elementary halogen. In that case, the halogen-free compounds are obtained by digestion or recrystallisation, for example from alcohols such as isopropanol. The chlorides and bromides obtained according to the process of the invention, can be converted into the corresponding iodides, fluorides, sulphates, tetrafluoborates, chlorates or acetates in a manner which is in itself known, by reaction with NaI, KF, $Na_2SO_4$, tetrafluoroboric acid, $KClO_3$ or sodium acetate.

The aminals obtainable according to the process of the invention can be converted to the corresponding aldehydes by alkaline or acid saponification. Hence, the aminals according to the invention offer a new important method of synthesis of aromatic aldehydes which is characterised in that the aminals obtainable according to the process of the invention, of the general formula I

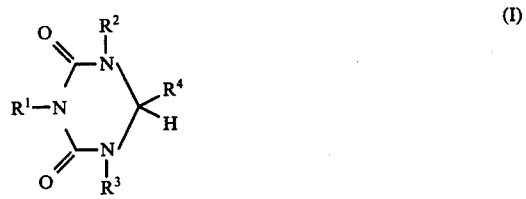

are subjected to an acid or alkaline hydrolysis. The aromatic aldehyde thereby formed has the general formula $R^{4'}$—CHO, wherein $R^4$ corresponds to the $R^4$ of the aminal employed.

The acid hydrolysis is in general carried out by reaction with concentrated mineral acid at elevated temperatures e.g. at about 60° to 100° C. Examples of mineral acids which may be mentioned are 80–100% strength sulphuric acid or phosphoric acid, and also concentrated hydrochloric acid.

For the hydrolysis, the acid is suitably employed in excess over the aminal, for example using about 5 to 20 mols per mol of the aminal employed, in which case the acid at the same time assumes the function of a solvent. In general, a reaction time of about 5–10 hours, depending on the temperature, is required for complete hydrolysis, in the course of which not only the desired aromatic aldehyde but also carbon dioxide and primary amines having the particular substituents $R^1$, $R^2$ and $R^3$ are formed. The hydrolysis mixture can be worked up in a manner which is in itself known. The hydrolysis by means of a concentrated mineral acid may be illustrated by the hydrolysis of 2,4-dioxo-hexahydro-1,3,5-trimethyl-6-(4-aminophenyl)-s-triazine:

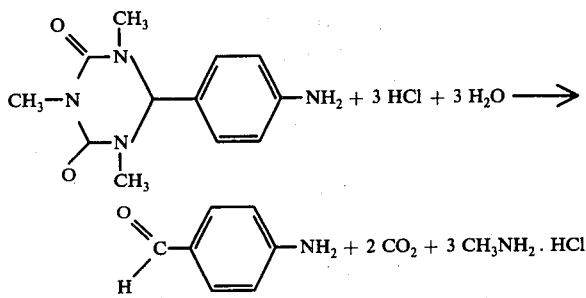

The alkaline hydrolysis is in general carried out by reaction with alkali metal hydroxides or alkali metal alcoholates at an elevated temperatures, e.g. at 80° to 150° C. Suitably, water or alcohols are employed as the solvent.

For the hydrolysis, the alkali metal hydroxide or the alcoholate is optionally employed in an amount of 4 to 10 mols, per mol of the aminal employed. In general, a reaction time of 2–10 hours, depending on the temperature, is required for complete hydrolysis, in the course of which not only the desired aromatic aldehyde but also alkali metal carbonate and primary amines having the particular substituents $R^1$, $R^2$ and $R^3$ are formed. The hydrolysis mixture can be worked up in a manner which is in itself known. The hydrolysis by means of alkali metal hydroxide may be illustrated by the hydrolysis of 2,4-dioxo-hexahydro-1,3,5-trimethyl-6-(2-methoxy-4-aminophenyl)-s-triazine:

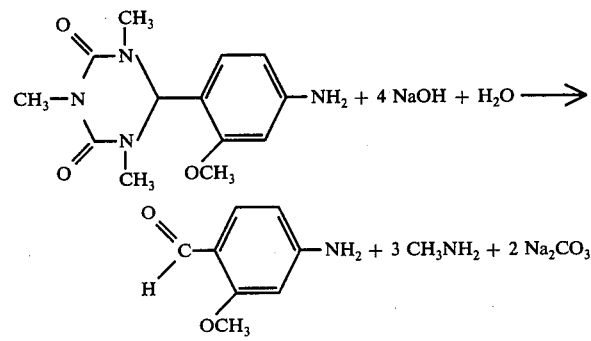

Using the process according to the invention, aromatic aldehydes which were hitherto only accessible with difficulty, such as, 4-amino-salicylaldehyde (A. A. Goldberg and R. S. Theobald Soc. 1954, 2641) can also be prepared easily. The latter aldehyde is, according to German pat. No. 1,296,121, an important intermediate product for the preparation of 3-heterocyclocoumarin derivatives, which are optical brighteners.

An important advantage of this method of synthesis of aromatic aldehydes is the fact that in contrast to the state of the art it permits the introduction of an aldehyde group, by a direct reaction, into aromatics which possess a free amino group as a further substituent. For example, 4-acetylaminosalicylaldehyde is accessible by means of this method of synthesis, in a simple manner and in substantially improved yields compared to those according to the state of the art (compare A. A. Goldberg et al, Soc. (London) 1954, 2641). 4-Acetylaminosalicylaldehyde is a known starting material for 3-(1')-triazolyl-(1,'2',3')-7-aminocoumarin, known as an optical brightener, which can be synthesised from 4-acetylaminosalicylaldehyde in a manner which is in itself known by methylating this compound at the free hydroxyl group by reaction with dimethyl sulphate and heating the methoxy derivative, thereby obtained, with 1,2,3-triazolyl-1-acetonitrile in ethanol as the solvent, in the presence of catalytic amounts of pyridine, and converting the methine compound thereby obtained, by heating in a suspension of anhydrous $AlCl_3$ in benzene, to the desired coumarin derivative. Analogously, it is also possible to synthetize analogous coumarin derivatives known as optical brighteners (compare German Pat. No. 1,296,121) by means of the triazinium salts according to the invention, via the substituted benzaldehydes or nephthaldehydes which are easily accessible thereby. The aminals according to the invention are thus to be regarded as a valuable starting material for the synthesis of these coumarin derivatives. The hydroxybenzaldehydes obtainable according to the process of the invention are important intermediates for the production of herbicides (see U.S. Pat. No. 3.503.732), antioxidants (see German Offenlegungsschrift No. 2.009.504), stabilizers for rubbers (see USSR Pat. No. 270,989) and polymerisation inhibitors (see USSR Pat. No. 264.387).

The following Examples illustrate the invention. Examples 1 to 14 illustrate the preparation of the aminals of the invention:

EXAMPLE 1

2,4-Dioxo-hexahydro-1,3,5-trimethyl-6-(4-aminophenyl)-s-triazine

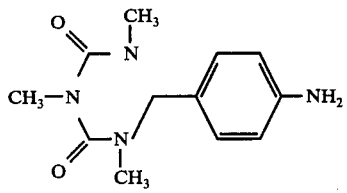

23.5 g (0.1 mol) of 2,4-dioxo-1,2,3,4-tetrahydro-1,3,5-trimethyl-s-triazinium bromide and 9.3 g (0.1 mol) of aniline in 50 ml of acetonitrile are heated to the boil. After 2 hours, the yellow precipitate which has separated out is filtered off, dissolved in water and neutralised with sodium carbonate solution. 19 g (77%) of 2,4-dioxohexahydro-1,3,5-trimethyl-6-(4-aminophenyl)-s-triazine of melting point 165°–167° C separate out.

Analysis $C_{12}H_{16}N_4O_2$ (248);
Calculated: C 58.1; H 6.4; N 26.6;
Found: C 58.3; H 6.2; N 26.5.

EXAMPLE 2

2,4-Dioxo-hexahydro-1,3,5-trimethyl-6-(4-dimethylaminophenyl)-s-triazine

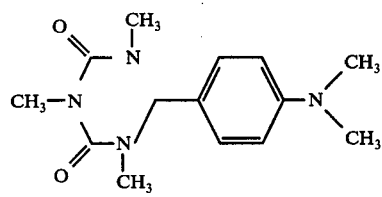

23.6 g (0.1 mol) of 2,4-dioxo-1,2,3,4-tetrahydro-1,3,5-trimethyl-s-triazinium bromide and 12.1 g (0.1 mol) of dimethylaniline are suspended in 50 ml of acetonitrile and stirred at room temperature. A clear solution results, from which a white precipitate separates out after 3 hours. This is dissolved in water and neutralised with sodium carbonate solution. 23 g (83%) of 2,4-dioxo-hexahydro1,3,5-trimethyl-6-(4-dimethylaminophenyl)-s-triazine of melting point 111° C–113° C separate out.

Analysis $C_{14}H_{20}N_4O_2$ (276);
Calculated: C 60.8; H 7.7; N 20.3;
Found: C 60.6; H 6.9; N 20.3.

EXAMPLE 3

2,4-Dioxo-hexahydro-1,3,5-trimethyl-6-(4-diethylaminophenyl)-s-triazine

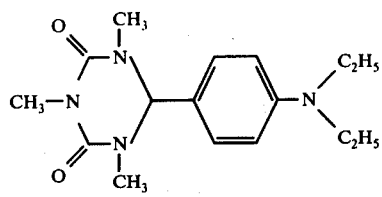

23.6 g (0.1 mol) of 2,4-dioxo-1,2,3,4-tetrahydro-1,3,5-trimethyl-s-triazinium bromide and 14.9 g (0.1 mol) of diethylaniline are stirred in 50 ml of acetonitrile. A clear solution results, from which a fresh precipitate separates out after a few hours. This is filtered off and dissolved in water. After neutralisation with sodium hydroxide, 24 g (79%) of 2,4-dioxo-hexahydro-1,3,5-trimethyl6-(4-diethylaminophenyl)-s-triazine are obtained as white crystals melting at 127°–129° C.

Analysis $C_{16}H_{24}N_4O_2$ (304);
Calculated: C 63.2; H 7.9; N 18.4;
Found: C 63.1; H 7.6; N 18.5.

EXAMPLE 4

2,4-Dioxo-hexahydro-1,3,5-trimethyl-6-(4-methylaminophenyl)-s-triazine

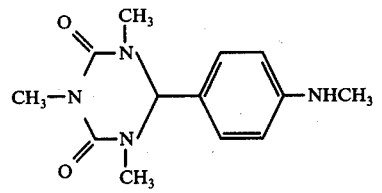

23.6 g (0.1 mol) of 2,4-dioxo-1,2,3,4-tetrahydro-1,3,5-trimethyl-s-triazinium bromide and 10.7 g (0.1 mol) of N-methylaniline are stirred in 50 ml of acetonitrile. A clear solution results, from which a fresh precipitate separates out after 3 hours. This is filtered off and dissolved in water. On neutralisation with sodium carbonate solution, 21 g (80%) of 2,4-dioxo-hexahydro-1,3,5-trimethyl-6-(4-diethylaminophenyl)-s-triazine separate out as white crystals which melt at 78°–80° C.

Analysis $C_{13}H_{18}N_{O2}$ (262);
Calculated: C 59.5; H 6.9; N 21.4;
Found: C 59.8; H 6.4; N 21.3.

EXAMPLE 5

2,4-Dioxo-hexahydro-1,3,5-trimethyl-6-(2-hydroxy-4-aminophenyl)-s-triazine

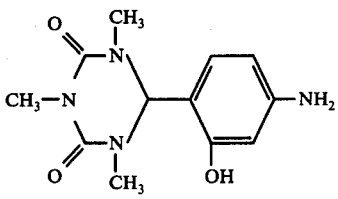

23.6 g (0.1 mol) of 2,4-dioxo-1,2,3,4-tetrahydro-1,3,5-trimethyl-s-triazinium bromide are dissolved in 50 ml of water and 10.9 g (0.1 mol) of m-aminophenol are added. After a few minutes, a clear solution has been produced. 8 g of sodium bicarbonate are added. Hereupon 25 g (89%) of 2,4-dioxo-hexahydro-1,3,5-trimethyl-6-(2-hydroxy-4-aminophenyl)-s-triazine separate out as white crystals which after dissolving in aqueous hydrochloric acid, clarification with active charcoal and neutralisation melt at 240° C.

Analysis $C_{12}H_{16}N_4O_3.H_2O$ (282);
Calculated: C 51.1; H 6.3; N 19.9;
Found: C 51.1; H 6.2; N 20.1.

EXAMPLE 6

2,4-Dioxo-hexahydro-1,3,5-trimethyl-6-(3-methyl-4-aminophenyl)-s-triazine

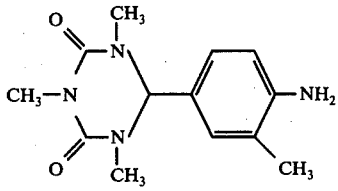

23.6 g (0.1 mol) of 2,4-dioxo-1,2,3,4-tetrahydro1,3,5-trimethyl-s-triazinium bromide and 10.7 g (0.1 mol) of o-toluidene in 50 ml of acetonitrile are heated to the boil for 5 hours. The mixture is then cooled and the precipitate which has separated out is filtered off. It is dissolved in water and the aqueous solution is rendered alkaline with sodium hydroxide solution (pH 8). Hereupon 21 g (80%) Of 2,4-dioxo-hexahydro-1,3,5-trimethyl-6-(3-methyl-4-aminophenyl)-s-triazine separate out as white crystals which melt at 151°–153° C.

Analysis $C_{13}H_{18}N_4O_2$ (262);
Calculated: C 59.5; H 6.9; N 21.4;
Found: C 59.3; H 6.91 N 21.2.

EXAMPLE 7

2,4-Dioxo-hexahydro-1,3,5-trimethyl-6-(3-chloro-4-aminophenyl)-s-triazine

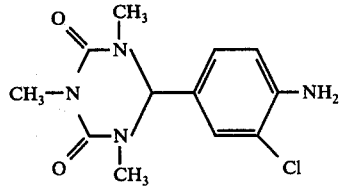

23.6 g (0.1 mol) of 2,4-dioxo-1,2,3,4-tetrahydro1,3,5-trimethyl-s-triazinium bromide and 11.8 g (0.1 mol) of 2-chloroaniline in 30 ml of dimethylformamide are stirred for 2 hours at 70° C. The mixture is then cooled and the white product which has separated out is filtered off. It is dissolved in water and the aqueous solution is neutralised with sodium hydroxide. An oil separates out, and solidifies after a few minutes. After filtration, 14 g (50%) of 2,4-dioxohexahydro-1,3,5-trimethyl-6-(3-chloro-4-aminophenyl)-s-triazine are obtained as white crystals which melt at 180°–182° C after recrystallisation from isopropanol.

Analysis $C_{12}H_{15}ClN_4O_2$ (282.5);
Calculated: C 51.0; H 5.3; N 19.8;
Found: C 51.0; H 5.5; N 19.9.

EXAMPLE 8

2,4-Dioxo-hexahydro-1,3,5-trimethyl-6-(2-methoxy-4-aminophenyl)-s-triazine

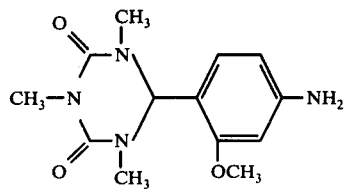

23.6 g (0.1 mol) of 2,4-dioxo-1,2,3,4-tetrahydro1,3,5-trimethyl-s-triazinium bromide and 12.4 g (0.1 mol) of 3-amino-1-methoxybenzene in 260 ml of acetonitrile are stirred for 6 hours. The precipitate which has separated out is then filtered off and dissolved in water. On neutralising the aqueous solution with potassium hydroxide solution, 24 g (87%) of 2,4-dioxo-hexahydro-1,3,5-trimethyl6-(2-methoxy-4-aminophenyl)-s-triazine separate out as white crystals which melt at 203°–205° C.

Analysis $C_{13}H_{18}N_4O_3$ (278);
Calculated: C 56.1; H 6.5; N 20.1;
Found: C 56.2 H 6.3; N 20.1.

EXAMPLE 9

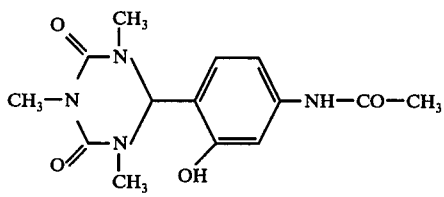

2,4-Dioxo-hexahydro-1,3,5-trimethyl-6-(2-hydroxy-4N-acetylaminophenyl)-s-triazine 12 g (0.08 mol) of m-acetylaminophenol, 18.8 g (0.8 mol) of 2,4-dioxo-1,2,3,4-tetrahydro-1,3,5-trimethyl-s-triazinium bromide and 8 g (0.08 mol) of triethylamine in 50 ml of acetonitrile are stirred for 9 hours. The precipitate which has separated out is then filtered off and stirred in water to remove the triethylamine hydrobromide. This leaves 16 g (65%) of 2,4-dioxo-hexahydro-1,3,5-trimethyl-6-(2-hydroxy-4-N-acetylaminophenyl)-s-triazine as white crystals which do not melt at temperatures up to 250° C.

Analysis $C_{14}H_{18}N_4O_4$ (306);
Calculated: C 54.9; H 5.9; N 18.3;
Found: C 55.1; H 5.7; N 18.2.

EXAMPLE 10

2,4-Dioxo-hexahydro-1,3,5-trimethyl-6-(4-hydroxynaphthyl)-s-triazine

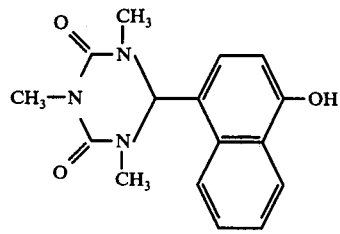

23.6 g (0.1 mol) of 2,4-dioxo-1,2,3,4-tetrahydro-1,3,5-trimethyl-s-triazinium bromide, 14.4 g (0.1 mol) of 1-naphthol and 10 g (0.1 mol) of triethylamine are stirred for 4 hours in 80 ml of acetone-nitrile. The white precipitate is then freed from the triethylamine hydrobromide by washing with water and 21 g (70%) of 2,4-dioxohexahydro1,3,5-trimethyl-6-(4-hydronaphthyl)-s-triazine are obtained as white crystals which melt at 209°–211° C after recrystallisation from methanol.

Analysis $C_{16}H_{17}N_3O_3$ (299);
Calculated: C 64.5; H 5.7; N 14.1;
Found: C 64.6; H 5.5; N 14.2.

EXAMPLE 11

2,4-Dioxo-hexahydro-1,3,5-trimethyl-6-(2-hydroxynaphthyl)-s-triazine

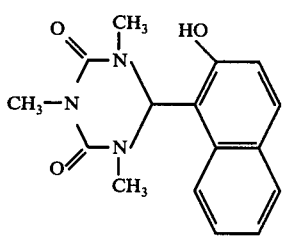

23.6 g (0.1 mol) of 2,4-dioxo-1,2,3,4-tetrahydro-1,2,3-trimethyl-s-triazinium bromide, 14.4 g (0.1 mol) of 2-naphthol and 10 g (0.1 mol) of triethylamine in 70 ml of acetonitrile are stirred for 4 hours. The precipitate formed is filtered off and purified by stirring in water. 26 g(87%) of 2,4-dioxo-hexahydro-1,3,5-trimethyl-6-(2-hydroxynaphthyl)-s-triazine are obtained as white crystals which after recrystallisation from methanol melt at 228° to 230° C.

Analysis $C_{16}H_{17}N_3O_3$
Calculated C 64.5; H 5.7; N 14.1;
Found C 64.7; H 5.6; N 14.1.

EXAMPLE 12

1,3-Diamino-4,6-bis-(2,4-dioxo-hexahydro-1,3,5-trimethyl-s-triazinyl-6)-benzene

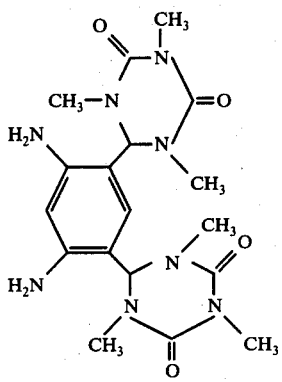

5.4 g (0.05 mol) of m-phenylenediamine are added to 23.6 g (0.1 mol) of 2,4-dioxo-1,2,3,4-tetrahydro-1,3,5-trimethyl-s-triazinium bromide in 50 ml of dimethylformamide. A white precipitate immediately separates out. This is filtered off and purified by stirring in aqueous sodium carbonate solution. 34 g (81%) of 1,3-diamino-4,6-bis-(2,4-dioxo-hexahydro-1,3,5-trimethyl-s-triazinyl-6)-benzene are obtained as white crystals which melt above 250° C.

Analysis $C_{18}H_{26}N_8O_4$ (1,418);
Calculated: C 51.7; H 6.2; N 26.8;
Found: C 51.3; H 6.3; N 26.4.

EXAMPLE 13

2,4-bis-(2,4-Dioxo-hexahydro-1,3,5-trimethyl-s-triazinyl-6)-phenol

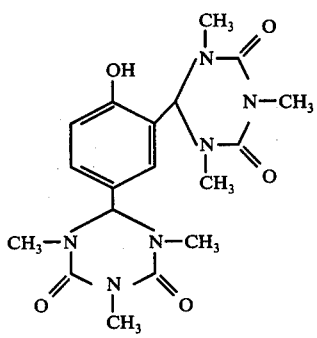

23.6 g (0.1 mol) of 2,4-dioxo-1,2,3,4-tetrahydro1,3,5-trimethyl-s-triazinium bromide in 50 ml of dimethylformamide are stirred with 10 g (0.1 mol) of triethylamine and 5.7 g (0.05 mol) of phenol for 9 hours at 70° C. The precipitate formed is then filtered off and purified by washing with water. This leaves 11 g (54%) of 2,4-bis-(2,4-dioxo-hexahydro-1,3,5-trimethyl-s-triazinyl-6)-phenol as white crystals melting above 250° C.

Analysis $C_{18}H_{24}N_6O_5$ (404);
Calculated: C 53.5; H 5.9; N 20.8;
Found: C 53.4; H 5.9; N 20.8.

EXAMPLE 14

2,4-Dioxo-hexahydro-1,3,5-trimethyl-6-(2-hydroxy-4-aminophenyl)-s-triazine 10.9 (0.1 mol) of m-aminophenol are added to a solution of 19.1 g (0.1 mol) of 2,4-dioxo-1,2,3,4-tetrahydro-1,3,5-trimethyl-s-triazinium chloride in 50 ml of water and the mixture is stirred for some minutes until a clear solution has been produced. 8 g of sodium bicarbonate are then added. 24 g (85) of the same compound as in Example 5 precipitate.

EXAMPLE 15

2,4-Dioxo-hexahydro-1,3,5-trimethyl-6-(4-hydroxy-2,6-di-tert.butyl-phenyl)-s-triazine.

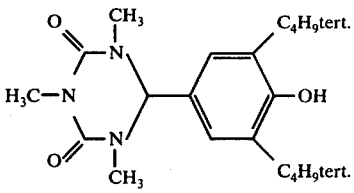

The solution of 47 g (0,2 mol) of 2,4-dioxo-1,3,5-tetrahydro-1,3,5-trimethyl-s-triazinium bromide, 41,2 g (0,2 mol) of 2,6-di-tert.butyl-phenol and 20 g ( 0,2 mol) of triethylamine in 150 ml of acetonitrile is heated under nitrogen for 7 hours at boiling temperature. After cooling the precipitate formed is filtered off, freed from triethylamine hydrobromide by washing with water and subsequently dried. There are obtained 56 g (77,5 % of theory) 2,4-dioxo-hexahydro-1,3,5-trimethyl-6(4-hydroxy-2,6-di-tert.butyl-phenyl)-s-triazine as white cristalls.

Melting point: 194° - 196° C (after recrystallization from toluene).

EXAMPLES 16 to 20 illustrate the hydrolysis of the aminals of the invention:

EXAMPLE 16

4-Aminosalicylaldehyde 113 g (0.4 mol) of 2,4-dioxo-hexahydro-1,3,5-trimethyl-6-(2-hydroxy-4-aminophenyl)-s-triazine in a solution of 120 g of potassium hydroxide in 640 ml of n-butanol are stirred for 3 hours at 100° C. The mixture is then cooled and the product filtered off. 67 g (96%) of 4-aminosalicylaldehyde are obtained as the potassium salt. 4-Acetylamio-Salicylaldehyde of melting point 186° C (A.A. Goldberg and R.S. Theobald, Soc. 1954, 2641) is obtained by simply stirring this salt in 150 ml of acetic anhydride at room temperature and then treating the product in boiling water.

EXAMPLE 17

4-Aminobenzaldehyde 24.7 g (0.1 mol) of 2,4-dioxo-hexahydro-1,3,5-trimethyl-6-(4-aminophenyl)-s-triazine in 100 ml of 37% strength aqueous hydrochloric acid are heated to 100° C for 5 hours. The mixture is then evaporated to dryness and the residue which remains is taken up in water. The aqueous solution is brought to pH 8 with sodium hydroxide solution and is extracted with three times 100 ml of either. After evaporation of the ether, 4-aminobenzaldehyde of melting point 71° C is obtained.

EXAMPLE 18

4-Dimethylaminobenzaldehyde 27.5 g (0.1 mol) of 2,4-dioxo-hexahydro-1,3,5-trimethyl-6-(4-dimethylaminophenyl)-s-triazine in 50 ml of 96% strength sulphuric acid are heated to 80° C for 6 hours. The solution is then poured onto ice and is rendered alkaline (pH 8 to 9) with sodium hydroxide solution. Hereupon 4-dimethylaminobenzaldehyde of melting point 74° C separates out.

EXAMPLE 19

4-Monomethylaminobenzaldehyde 26.1 g (0.1 mol) of 2,4-dioxo-hexahydro-1,3,5-trimethyl-6(4-methylaminophenyl)-s-triazine and 16 g (0.4 mol) of sodium hydroxide in 50 ml of water are stirred for 8 hours at 95° C. The solution is cooled and extracted by shaking with three times 100 ml of methylene chloride. After evaporation of the methylene chloride solution, 4-methylaminobenzaldehyde of melting point 58° C remains.

EXAMPLE 20

2-Hydroxy-naphthaldehyde 29.7 g (0.1 mol) of 2,4-dioxo-hexahydro-1,3,5-trimethyl-6-(2-hydroxy-naphthyl)-s-triazine and 20 g (0.5 mol) of sodium hydroxide in 50 ml of water are stirred for 8 hours at 95° C. The solution is then acidified and 2-hydroxy-naphthaldehyde of melting point 82° C is obtained.

The preparation of the starting materials is illustrated in the following Examples:

EXAMPLE 21

(a) 2,4-Dioxo-1,2,3,4-tetrahydro-1,3,5-trimethyl-s-triazinium bromide, which is employed as the starting material for Examples 1 to 15, is obtained as follows:

15.7 g (0.1 mol) of 2,4-dioxo-hexahydro-1,3,5-trimethyl-s-triazine are dissolved in 30 ml of methylene chloride and 24 g (0.15 mol) of bromine are added dropwise whilst keeping the temperature at between 20° C and 30° C by cooling. After a few minutes, the addition product of bromine with 2,4-dioxo-1,2,3,4-tetrahydro-1,3,5-trimethyl-s-triazinium bromide separates out in the form of orange-coloured crystals. These are filtered off and recrystallised from isopropanol. 20 g (85%) of 2,4-dioxo-1,2,3,4-tetrahydro-1,3,5-trimethyl-s-triazinium bromide are obtained as white crystals which melt at 217° C.

Analysis $C_6H_{10}BrN_2O_2$ (236);
Calculated: C 30.6; H 4.2; N 17.8;
Found: C 30.9; H 4.4; N 17.8.

The following triazinium salts can also be employed as starting materials, analogously to the description in Examples 1 to 15.

(b) 2,4-Dioxo,1,2,3,4-tetrahydro-1,5-diethyl-3-methyl-s-triazinium bromide 18.5 g (0.1 mol) of 2,4-dioxo-hexahydro-1,5-diethyl-3-methyl-s-triazine are dissolved in 20 ml of methylene chloride and 24 g (0.15 mol) of bromine are added dropwise. The temperature is kept at 20° C to 30° C by occasional cooling. After a few minutes, an orange-coloured precipitate separates out. This is filtered off and recrystallised from isopropanol. 23 g (87%) of 2,4-dioxo-1,2,3,4-tetrahydro-1,5-diethyl-3-methyl-s-triazinium bromide of melting point 198° C are obtained.

Analysis $C_8H_{14}BrN_3O_2$ (264);
Calculated: C 36.4; H 5.3; N 15.9;
Found: C 36.3; H 5.3; N 15.5.

(c) 2,4-Dioxo-1,2,3,4-tetrahydro-1,5-dicyclohexyl-3-methyl-s-triazinium bromide 29.3 g (0.1 mol) of 2,4-dioxo-hexahydro-1,5-dicyclohexyl-3-methyl-s-triazine are initially introduced into 40 ml of methylene chloride and 24 g (0.15 mol) of bromine are added dropwise. The temperature is kept at 20° C to 30° C by cooling. The orange-red precipitate which has separated out is filtered off and recrystallised from isopropanol. 25 g (67%) of 2,4-dioxo-1,2,3,4-tetrahydro-1,5-dicyclohexyl-3-methyl-s-triazinium bromide of melting point 250° C are obtained.

Analysis $C_{16}H_{26}BrN_3O_2$ (372);
Calculated: C 51.6; N 6.9; N 11.3;
Found: C 51.6; H 6.9; N 11.3.

(d) 2,4-Dioxo-1,2,3,4-tetrahydro-1,5-dimethyl-3-isopropyl-s-triazinium bromide 18.5 g (0.1 mol) of 2,4-dioxo-hexahydro-1,5-dimethyl-3-isopropyl-s-triazine are dissolved in 20 ml of methylene chloride and 24 g (0.15 mol) of bromine are added dropwise. After one hour, the orange-coloured precipitate which has separated out is filtered off and recrystallised from isopropanol. 20 g (75%) of 2,4-dioxo-1,2,3,4-tetrahydro-1,5-dimethyl-3-isopropyl-s-triazinium bromide of melting point 212°–214° C are obtained.

Analysis $C_8H_{14}BrN_3O_2$ (264);
Calculated: C 36.4; H 5.3; N 15.9;
Found: C 36.2; H 5.3; N 16.0.

(e) 2,4-Dioxo-1,2,3,4-tetrahydro-1,5-diisopropyl-3-methyl-s-triazinium bromide 21.3 g (0.1 mol) of 2,4-dioxo-hexahydro-1,5-diisopropyl-3-methyl-s-triazine are dissolved in 30 ml of methylene chloride and 24 g (0.15 mol) of bromine are added dropwise. The temperature is kept at 20° C to 30° C by cooling. After one hour, the orange-coloured precipitate which has formed is filtered off and recrystallised from isopropanol. 16 g (55%) of 2,4-dioxo-1,2,3,4-tetrahydro-1,5-diisopropyl-3-methyl-s-triazinium bromide are obtained as white crystals which melt at 210°–212° C.

Analysis $C_{10}H_{18}BrN_3O_2$ (292);
Calculated: C 41.1; H 6.2; H 14.4;
Found: C 41.3; H 6.1; N 14.2.

(f) 2,4-Dioxo-1,2,3,4-tetrahydro-1,5-dibenzyl-3-methyl-s-triazinium bromide 30.9 g (0.1 mol) of 2,4-dioxo-hexahydro-1,5-dibenzyl-3-methyl-s-triazine are initially introduced into 40 ml of methylene chloride and 24 g (0.1 mol) of bromine are added whilst cooling. The yellow crystals which hereupon precipitate are stirred into isopropanol. They dissolve and after few minutes the solution turns colourless. On cooling, white crystals separate out. After filtering off, 21 g (53%) of 2,4-dioxo-1,2,3,4-tetrahydro-1,5-dibenzyl-3-methyl-3-triazinium bromide of melting point 164°–166° C are obtained.

Analysis $C_{18}H_{18}BrN_3O_2$ (388);
Calculated: C 55.5; H 4.6; N 10.8;
Found: C 55.3; H 5.0; N 10.6.

(g) 2,4-Dioxo-1,2,3,4-tetrahydro-1,3,5-trimethyl-s-triazinium chloride 15.7 g (0.1 mol) of 2,4-dioxo-hexahydro-1,3,5-trimethyl-s-triazine are dissolved in 50 ml of water. 7 g (0.1 mol) of chloride are slowly passed into this solution. The temperature is kept at 25 –30° C by occassional cooling. The aqueous solution is then evaporated in vacuo, and 18 g (94%) of 2,4-dioxo-1,2,3,4-tetrahydro--1,3,5-s-triazinium chloride are thereby obtained as white crystals, which are strongly hygroscopic.

(h) 2,4-Dioxo-1,2,3,4-tetrahydro-1,3,5-trimethyl-s-trimethyl-s-triazine are dissolved in 30 ml of methylene chloride and 13.4 g (0.1 mol) of sulphuryl chloride are added dropwise. Stirring is continued until the evolution of gas has ceased, and the methylene chloride is then evaporated in vacuo. The same compound as in Example g is obtained (i) 2,4-Dioxo-1,2,3,4-tetrahydro-1,3,5-trimethyl-s-triazinium chloride 17.8 g (0.1 mol) of sodium dichlorocyanuric acid are added to 15.7 g (0.1 mol) of 2,4-dioxo-hexahydro-1,3,5-trimethyl-s-triazine in 50 ml of methanol and the mixture is stirred. The cyanuric acid which has precipitated is then filtered off and the filtrate is evaporated. The residue which remains on evaporation is digested with water. After renewed filtration to remove residual cyanuric acid, an aqueous solution of the same compound as in Example g is obtained.

EXAMPLE 22

The 2,4-dioxo-hexahydro-s-triazines used as the starting material for Examples 21(a) to (i) can be prepared as follows:

2.4-Dioxo-hexahydro-1,3,5-s-triazine 145 g ( 1 mol) of 1,3,5-trimethyl-biuret and 30 g of paraformaldehyde are heated with 5 ml of concentrated hydrochloric acid to 70° C for 5 hours. The liquid contents of the flask are then poured onto a drying tray and after having solidified are recrystallised from cyclohexane. 154 g (98%) of 2,4-dioxo-hexahydro-1,3,5-s-triazine of melting point 88°–90° C are obtained.

Analogously, 1,5-diethyl-3-methyl-biuret and paraformaldehyde gave 2,4-dioxo-hexahydro-1,5-diethyl-3-methyl-s-triazine as a colourless oil, 1,5-dicyclohexyl-3-methyl-biuret and paraformaldehyde at 100° C gave 2,4-dioxo-hexahydro-1,5-dicyclohexyl-3-methyl-s-triazine as a viscous oil, 1,5-dimethyl-3-isopropyl-biuret and paraformaldehyde at 100° C gave 2,4-dioxo-hexahydro-1,5-dimethyl-3-isopropyl-s-triazine as white crystals of melting point 53°–54° C, 1,5-diisopropyl-3-methyl-biuret and paraformaldehyde at 100° C in the presence of gaseous hydrogen chloride gave 2,4-dioxohexahydro-1,5-diisopropyl-3-methyl-s-triazine as a brown oil and 1,5-dibenzyl-3-methyl-biuret and paraformaldehyde gave 2,4-dioxo-hexahydro-1,5-dibenzyl-3-methyl-s-triazine as a yellow viscous oil.

What is claimed is:

1. A compound of the formula

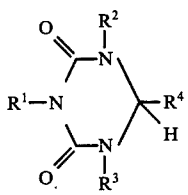

wherein

R$^1$, R$^2$ and R$^3$ are the same or different and are unsubstituted C$_{1-18}$ alkyl, C$_2$–C$_{10}$ alkenyl, C$_{5-12}$ cycloalkyl or substituted C$_{1-18}$ alkyl, C$_2$–C$_{10}$ alkenyl, C$_{5-12}$ cycloalkyl where the substituent is a halogen atom, a nitrile group, phenyl, substituted phenyl where the substituent is C$_{1-4}$ alkyl, cyano, halogen or C$_{1-4}$ alkoxy, a C$_1$–C$_4$ alkoxy group or a carb-C$_1$–C$_4$-alkoxy group, phenyl, naphthyl or substituted phenyl where the substituent is a C$_1$–C$_4$ alkyl group, a halogen atom, substituted C$_1$–C$_4$ alkyl group, a nitrile group, a C$_1$–C$_4$ alkoxy group or a carb-C$_1$–C$_4$-alkoxy group and R$^4$ is monosubstituted or polysubstituted phenyl or naphthyl containing at least one substituent of the group of C$_1$–C$_6$ alkyl, C$_1$–C$_6$ acylamino, hydroxy, C$_1$–C$_4$ alkoxy, amino or a substituted amino where the substituent is a C$_1$–C$_6$ alkyl radical.

2. A compound of claim 1 wherein R$^1$, R$^2$ and R$^3$ are the same or different and are C$_1$–C$_4$ alkyl or C$_5$–C$_6$ cycloalkyl, either of which may be substituted by phenyl and R$^4$ is mono- or polysubstituted phenyl or naphthyl.

3. Process for preparing a compound having the formula

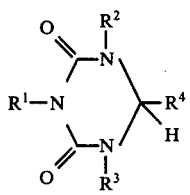

wherein

R$^1$, R$^2$ are R$^3$ are the same or different and are unsubstituted C$_{1-18}$ alkyl, C$_2$–C$_{10}$ alkenyl, C$_{5-12}$ cycloalkyl or substituted C$_{1-18}$ alkyl, C$_2$–C$_{10}$ alkenyl, C$_{5-12}$ cycloalkyl where the substituent is a halogen atom, a nitrile group, phenyl, substituted phenyl where the substituent is C$_{1-4}$ alkyl, cyano, halogen or C$_{1-4}$ alkoxy, a C$_1$–C$_4$ alkoxy group or a carb-C$_1$–C$_4$-alkoxy group, phenyl, naphthyl or substituted phenyl where the substituent is a C$_1$–C$_4$ alkyl group, a halogen atom, substituted C$_1$–C$_4$ alkyl group, a nitrile group, a C$_1$–C$_4$ alkoxy group or a carb-C$_1$–C$_4$-alkoxy group and R$^4$ is monosubstituted or polysubstituted phenyl or naphthyl containing at least one substituent of the group of C$_1$–C$_6$ alkyl, C$_1$–C$_6$ acylamino, hydroxy, C$_1$–C$_4$ alkoxy, amino or a substituted amino where the substituent is a C$_1$–C$_6$ alkyl radical which comprises contacting (a) 2,4-dioxo-1,2,3,4-tetrahydro-1,3,5-triazinium salt having the formula

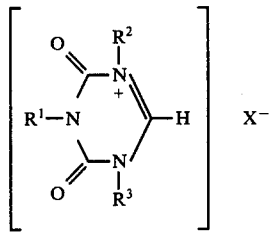

(II)

wherein

X− is chloride or bromide ion and

R$^1$, R$^2$ and R$^3$ are as defined above with an aromatic compound of the formula

R$^4$— H wherein

R$^4$ is a defined above.

4. Process of claim 3 wherein 2,4-dioxo-1,2,3,4-tetrahydro-1,3,5-triazinium salts are used wherein R$^1$, R$^2$ and R$^3$ are the same or different and are C$_1$–C$_4$ alkyl or C$_5$–C$_6$ cycloalkyl either of which may be substituted by phenyl and R$^4$ is mono- or polysubstituted phenyl or naphthyl.

* * * * *

UNITED STATES PATENT AND TRADEMARK OFFICE
CERTIFICATE OF CORRECTION

PATENT NO. : 4,080,502

DATED : March 21, 1978

INVENTOR(S) : Florin Seng et al

It is certified that error appears in the above-identified patent and that said Letters Patent are hereby corrected as shown below:

Column 2, line 5, "mono:" should read -- mono- --.

Column 2, line 23, "nitrile" should read -- nitril --.

Column 3, line 17, "2naphthol" should read -- 2-naphthol --.

Column 3, line 47, "animals" should read -- aminals --.

Column 4, line 20, "ivention" should read -- invention --.

Column 5, line 47, "1,5di-" should read -- 1,5-di- --.

Column 8, line 13, "nephthaldehydes" should read
-- naphthaldehydes --.

Column 8, line 51, "H 6.2" should read -- H 6.1 --.

Column 9, line 4, insert -- - -- after "hexahydro".

Column 9, line 31, insert -- - -- after "trimethyl".

Column 9, line 40, insert -- N- -- after "4-".

Column 9, line 61, "$C_{13}H_{18}N_{o2}$" should read -- $C_{13}H_{18}N_4O_2$ --.

Column 10, line 36, insert -- - -- after "tetrahydro".

Column 10, line 49, "H 6.91" should read -- H 6.9 --.

Column 10, line 63, insert -- - -- after "tetrahydro".

Column 11, line 24, insert -- - -- after "tetrahydro".

Column 11, line 32, insert -- - -- after "trimethyl".

UNITED STATES PATENT AND TRADEMARK OFFICE
CERTIFICATE OF CORRECTION

PATENT NO. : 4,080,502
DATED : March 21, 1978
INVENTOR(S) : Florin Seng et al

It is certified that error appears in the above–identified patent and that said Letters Patent are hereby corrected as shown below:

Column 11, lines 49-50, delete the two lines following the formula in Example 9 and insert them before the heading "EXAMPLE 9".

Column 11, line 49, insert -- - -- after "4"

Column 11, lines 66-67, insert -- - -- after "hydroxy".

Column 12, line 21, insert -- - -- after "dioxohexahydro".

Column 12, line 33-34, insert -- - -- after "hydroxy".

Column 13, line 49, insert -- - -- after "tetrahydro".

Column 14, line 1, "(85)" should read -- (85%) --.

Column 14, line 25, "-6(4-" should read -- -6-(4- --.

Column 14, line 43, "Acetylamio" should read -- Acetylamino --.

Column 15, line 7, insert -- - -- after "6".

UNITED STATES PATENT AND TRADEMARK OFFICE
CERTIFICATE OF CORRECTION

PATENT NO. : 4,080,502

DATED : March 21, 1978

INVENTOR(S) : Florin Seng et al

It is certified that error appears in the above-identified patent and that said Letters Patent are hereby corrected as shown below:

Column 16, line 55, "chloride" should read -- chlorine --.

Signed and Sealed this

Twenty-sixth Day of September 1978

[SEAL]

Attest:

RUTH C. MASON
Attesting Officer

DONALD W. BANNER
Commissioner of Patents and Trademarks